United States Patent [19]

Relyveld

[11] Patent Number: 5,318,913
[45] Date of Patent: Jun. 7, 1994

[54] REAGENT FOR THE DETERMINATION BY HEMAGGLUTINATION OF ANTIBODIES TO BACTERIAL TOXINS, METHOD OF PREPARATION AND APPLICATION THEREOF

[75] Inventor: Edgar H. Relyveld, 3 place du Général Stéfanik, 75016 Paris, France

[73] Assignee: Edgar H. Relyveld, Paris, France

[21] Appl. No.: 420,345

[22] Filed: Oct. 12, 1989

Related U.S. Application Data

[63] Continuation of Ser. No. 826,065, Feb. 4, 1986, abandoned.

[30] Foreign Application Priority Data

Feb. 5, 1985 [FR]   France .................... 80 01579

[51] Int. Cl.$^5$ .................. G01N 33/556; G01N 33/569
[52] U.S. Cl. ..................... 436/520; 436/521; 436/532; 436/808; 435/7.32; 435/975; 435/967
[58] Field of Search ............ 436/520, 521, 532, 808, 436/809; 435/4, 41, 842, 844, 7.32, 975

[56] References Cited

U.S. PATENT DOCUMENTS 4,403,037   9/1983   Coates ........................ 436/521
4,569,919   2/1986   Toth et al. .................. 436/533

FOREIGN PATENT DOCUMENTS 2478470   9/1981   France .

OTHER PUBLICATIONS

Relyveld et al., "Preparation of vaccines using glutaraldehyde", Chemical Abstracts, vol. 83, Abstract No. 65363d, p. 437 (1975).
Sundick et al., "Agglutination Reactions", Methods in Immunodiagnosis, Rose & Bigazzi, Eds., 1980, pp. 109–127.

*Primary Examiner*—Carol E. Bidwell
*Attorney, Agent, or Firm*—Bierman and Muserlian

[57] ABSTRACT

The invention relates to a method of preparing a reagent for the determination by hemagglutination of antibodies to bacterial toxins. According to this method erythrocytes are treated with glutaraldehyde and then with the bacterial toxins in the presence of glutaraldehyde without a wash step. The reagent thus obtained is further treated with a reagent for blocking aldehyde groups.

16 Claims, No Drawings

REAGENT FOR THE DETERMINATION BY HEMAGGLUTINATION OF ANTIBODIES TO BACTERIAL TOXINS, METHOD OF PREPARATION AND APPLICATION THEREOF

PRIOR APPLICATION

This application is a continuation of U.S. patent application Ser. No. 826,065 filed Feb. 4, 1986, now abandoned.

FIELD OF THE INVENTION

The present invention relates to a new reagent, consisting of coupled erythrocytes, by means of which antibodies to bacterial toxins may be determined by hemagglutination, to the method of preparing this reagent, and also to the kit of reagents necessary for carrying out the determination and the corresponding method of determination.

BACKGROUND OF THE ART

It is known to determine antibodies using hemagglutination to visualize their presence in a biological medium; for this purpose, erythrocytes are used which bear an antigen which reacts with the antibodies to be determined; however, the treated erythrocytes have poor stability, and this is a major disadvantage of this type of method, which is in other respects useful because it does not demand the use of expensive measuring apparatus. In French Patent A-2,331,352, a means is described for improving, in particular, the stability of the hemagglutination reagent, consisting in treating the erythrocytes, suspended in a buffer, with a lower aliphatic aldehyde and a water-soluble chromium salt before they are brought into contact with the chosen antigen; the storage period is then improved if the treated erythrocytes are stored at 4° C. in a colloidal solution or in the lyophilized state. In French Patent A-2,475,737, there is a description of another means for improving the stability of red cells treated for use as a reagent in hemagglutination reactions, and which simultaneously decreases the phenomena of spontaneous agglutination; whole blood is subjected to the action of an aldehyde, such as formaldehyde or glutaraldehyde, and the red cells are then isolated and treated with a tannin before they are brought into contact with the chosen antigen to obtain a reagent which will be stored in lyophilized form.

SUMMARY OF THE INVENTION

A new reagent has now been found for the determination by hemagglutination of antibodies to bacterial toxins, the reagent being especially stable, very sensitive, devoid of all toxicity, and hence capable of being handled without special precautions: the technique of determination is, moreover, simple and rapid, and applicable in the field using small blood samples.

According to the invention, the reagent, which consists of erythrocytes sensitized to the antigen corresponding to the antitoxin to be determined, is prepared by reacting glutaraldehyde with an aqueous suspension of erythrocytes, in such a way that the latter are not hemolized when they are subsequently brought into contact with the bacterial toxin corresponding to the antibodies to be determined, and then by treating these erythrocytes with a certain quantity of the bacterial toxin in the presence of glutaraldehyde, to bind the toxin to the erythrocytes and simultaneously modify its structure in such a way that it loses its toxicity for man or animals without denaturation of its antigenic sites.

DETAILED DESCRIPTION

In French Patent A-2,478,470, a method has already been described for preparing immunogenic cells resulting from the binding of different agents, such as antigens, hormones or toxins, to lymphocytes by the action of glutaraldehyde on a mixture of the lymphocytes and the immunogenic agents; in the case of the binding of tetanus toxin and diphtheria toxin, the cell preparations thereby obtained were detoxified. However, it was not certain that, by application of a process of this kind to cells as fragile as erythrocytes, a reagent for determination by hemagglutination would be obtained which was stable, non-toxic, non-agglutinating and sensitive. The stability of the sensitized red cells used in determinations by hemagglutination is a genuine problem, and some of the solutions previously found have been mentioned above; it is surprising that none of the more or less complex treatments previously recommended is required for the reagent of the invention. Moreover, for hemagglutination to serve as a visualization reaction in a method of determination, it has to take place even in the presence of small amounts of antibodies, and without spurious agglutination; now, it was not possible to deduce from the above document that the detoxified toxins bound to the erythrocytes would still be sufficiently antigenic to permit determination of an antibody at low concentration in biological media.

In a preferred embodiment of the invention, the method for obtaining the reagent involves an additional stage which consists in treating the red cells bearing the detoxified toxin with a compound bearing a group capable of reacting with the free aldehyde groups; the blocking of the aldehyde groups resulting therefrom further improves the stability of the reagent, decreases spurious hemagglutinations due to reactions with the various proteins present in the sample to be assayed, which increases the sensitivity of the reagent, and finally eliminates any risk of toxic activity reappearing as a result of partial reversion of the detoxified structures in the bacterial toxin during storage of the reagent. As a blocking agent, amino acids such as glycine or lysine, peptones such as meat peptones and case in hydrolysate, and primary amines such as glycine and ethanolamine may be mentioned.

Among the bacterial toxins which can be coupled to erythrocytes by the method according to the invention, diphtheria toxin and tetanus toxin may be mentioned; it is preferable that these toxins should be of high purity for coupling to the red cells; for example, crystallized diphtheria toxin, dialyzed against the buffered aqueous solution used for suspending the cells, is used for the reaction.

It is preferable to use nucleated red cells of birds such as pigeons and turkeys, the sedimentation of which is known to be faster than that of sheep red cells, for preparing the reagents of the invention. In this manner, a determination using the method of the invention can be carried out in approximately 15 minutes, whereas with the techniques currently employed, it is necessary to wait several hours before reading the results.

In a particular embodiment of the invention, glutaraldehyde will be reacted at room temperature for a few minutes with bird erythrocytes suspended in an isotonic buffered solution having an approximate pH of between 6.5 and 8.0. The buffer solution can be an aqueous saline phosphate solution, in which erythrocytes will be suspended to obtain a concentration of 1 to 12% (v/v); glutaraldehyde is then introduced in the form of a dilute aqueous solution to obtain a final aldehyde concentration of 0.001 to 0.1M in the solution containing the erythrocytes. The erythrocytes can also be added to a buffered aqueous solution of glutaraldehyde, of concentration between 0.0025M and 0.25M, to obtain the same final concentrations.

At this stage, it is not necessary to isolate the erythrocytes, and the bacterial toxin can be introduced directly into the suspension; for this purpose, a solution of toxin in the same buffer, at an approximate concentration of between 4 mg and 20 mg/ml, is added in the proportion of 0.4 mg to 2 mg of toxin per ml of erythrocytes to be treated. To carry out the coupling and detoxification of all the toxin added, the mixture must be maintained preferably for at least one hour, or 2 to 3 hours depending on the toxins to be bound, at room temperature. The sensitized cells are then isolated by centrifugation and washed with an isotonic buffered aqueous solution.

To saturate the free aldehyde groups, the cells thereby obtained are suspended for at least 15 minutes in a buffered solution of the chosen blocking agent, at an approximate concentration of 0.1M to 1M, in the proportion of one volume of erythrocytes for 7 volumes of solution. After the usual rinses, the erythrocytes isolated by centrifugation can be resuspended in an isotonic buffered aqueous solution in the presence of one of the usual bactericidal agents, such as sodium azide or merthiolate at a final concentration of 1:5000 and 1:10000 (w/v), respectively, and stored as they are at 4° C. for more than a year or at at 37° C. for nearly a month; lyophilization of this suspension can also be carried out, but it is nevertheless preferable not to lyophilize, since it is known that, while the storage of the reagent is thereby improved, its properties are frequently modified during this operation, and in a non-reproducible manner.

The contact times of the reagents in the various stages of the method depend on the temperature at which the treatment is carried out, and also on the concentration of the reagents in the solution and their relative amounts, and these various parameters may be suitably adjusted by the specialist.

The reagents obtained by this method form another subject of the invention. They are comprised of corpuscles, which are non-toxic, this being an advantage of the invention, consisting of erythrocytes to which bacterial toxins have been bound through the agency of glutaraldehyde. The aldehyde groups on these corpuscles can, optionally, have been saturated by chemical reaction with a blocking agent; in the case of reagents based on diphtheria toxin, saturation of the aldehyde groups is highly desirable.

The reagents of the invention are advantageously used for the determination of antibodies directed against the corresponding bacterial toxins present in biological fluids, without samples having undergone prior treatment by dialysis, centrifugation, precipitation or the like; simple dilution with water will generally be sufficient. This is one of the advantages of the invention, the importance of which must be emphasized. In effect, none of the methods currently employed for determining antitetanus or antidiptheria antibodies permit whole blood to be used; thus, since only serum can be used, a large sample of blood, at least a few ml, must be drawn from the individual in whom it is desired to determine the degree of protection against diphtheria or tetanus, the sample being sufficiently large to enable the serum to be separated by centrifugation. Although this procedure is common, it can only be carried out by qualified personnel and with expensive equipment. With the reagents of the invention, a sample consisting of a single drop of blood is sufficient to carry out a determination of the antibodies by the method of determination of the invention.

This method of determination consists in mixing different dilutions of the sample to be studied, in a buffered aqueous solution at a pH of between 6.5 and 8, with a specified amount of a reagent of the invention, and then observing, after 15 minutes at room temperature, and preferably after 20 minutes, at what dilutions hemagglutination takes place; the antibody concentration in the sample is then determined by reference to a standard. As mentioned above, the sample can be fresh blood or blood stored with an anticoagulant or absorbed on an absorbent material such as a blotting-paper of the type used in biology, serum or alternatively an antibody preparation originating from an immunized animal. When an investigation is carried out to find out whether an individual has an antibody level sufficient for protection against diphtheria or tetanus, the blood is diluted beforehand approximately 20-fold in distilled water or weakly acidified water; under these conditions, the lysed red cells and the blood proteins do not interfere.

For serum, the starting dilution will generally be 1/10 or 1/20; successive dilutions can then be prepared, for example, according to a geometric progression with a common ratio of 2.

If the assay is performed by introducing the reagent composition and the different dilutions of the sample into the cups of a polystyrene plate containing at least 8 wells, 10 $\mu$l of biological fluid sample suffice for performing a determination, and this is a considerable advantage of the invention. In the case of the determination of antidiphtheria antibodies, it is preferable to add a protein, such as human serum albumin (HSA), or another component of high molecular mass such as polyvinylpyrrolidone, into the determination medium so that the sensitivity of the method is comparable to that obtained for the determination of antitetanus antibodies; the serum albumin can be introduced at the same time as the reagent composition, by mixing the latter with a buffered solution of HSA.

Under these conditions, it is possible to detect reproducibly the presence of 0.003 to 0.0004 international antitoxin units (IAU) in whole blood.

The reagent composition used can be the suspension of sensitized erythrocytes which has served for the storage thereof, that is to say a buffered aqueous suspension at an approximate pH of between 6.5 and 8.0, containing from 1% to 20% (v/v) of coupled erythrocytes; no prior treatment of the storage suspension is necessary, and a reagent kit, which is a subject of the invention, can contain this suspension with a certain volume of buffered aqueous solution for dilution, a reference serum and a note of the minimum antibody concentration giving observable hemagglutination, that is to say the concentration at which the red cells settle in the form of a uniform network distributed over the entire surface of the walls, and not as a pellet of small diameter. The reagent composition used can also be prepared instantaneously or a short time before the assay by resuspension of the lyophilized sensitized erythrocytes.

It will be understood from reading the foregoing that the method of determination according to the invention is easy to carry out, cheap, especially because it does not require any complicated measuring apparatus, and rapid, since the reading of the microtest plate can be carried out less than 20 minutes after the introduction of the sample, that it can be performed in the absence of refrigeration sources, since the reagents are not modified after several weeks at room temperature, and performed some time after the sample has been drawn, since the antibody titer of a specimen of whole blood is not modified after a 10-μl sample has been stored on a disk at blotting-paper 2 mm in diameter for one week at room temperature and several weeks at 4° C.

The invention is illustrated by examples of implementation of the preparation method of the invention for obtaining erythrocytes sensitized to tetanus toxoid and diphtheria toxoid, and also by examples of titration of the antibodies present in blood with reagents of the invention.

EXAMPLE 1

Coupling of tetanus toxin or diphtheria toxin to Erythrocytes

Turkey red cells collected in Alsever's solution are washed with isotonic phosphate buffer at pH 7.4 containing NaCl (PBS), and then suspended in the same buffer in the proportion of 3.6 ml of red cells for a final volume of 100 ml of phosphate buffer (pH 7.4). 100 ml of this suspension, 71.5 ml of a 0.025M solution of glutaraldehyde in the same buffer are added slowly with stirring. After one minute of contact, 71.5 ml of a solution of tetanus toxin or diphtheria toxin in the same buffer, containing 4 mg of toxin per ml, are introduced. The mixture is stirred for one hour for tetanus toxin and 2 hours for diphtheria toxin, at room temperature, and the sensitized red cells are then separated by centrifugation and washed 3 times with an equal volume (243 ml) of the same buffer.

An equal volume of a 0.1M solution of glycine in the same phosphate buffer is then poured onto the centrifugation pellet, and the suspension is left stirring for 30 minutes. The red cells thus treated are isolated by centrifugation, and washed 3 times with the same volume of phosphate buffer PBS before being resuspended, in the proportion of 5 ml of sensitized red cells for 100 ml of buffer, in PBS containing 2:10,000 (w/v) of sodium azide.

It is important to use a buffer of only weakly alkaline pH; thus, the results obtained with a buffer of ph 8.65 are negative.

EXAMPLE 2

Determination of antidiphtheria antibodies in a reference human serum

The reference serum, containing 1 IAU/ml, is diluted to 1/10, and then by doubling dilutions up to 1/2560, in the cups of a microtest plate containing 50 μl of PBS.

In an initial assay, 50 μl of sensitized red cell suspension are then introduced into each cup. In a second assay, 50 μl of a 1% suspension of the sensitized red cells in PBS also containing 0.1% of human serum albumin are introduced into each cup. The appearance of the wells is observed after 20 minutes of contact at room temperature, the microtest plate having been covered to prevent evaporation.

The results obtained are given in Table I below, and show that, in the absence of albumin, the determination of the limiting dilution is virtually impossible.

TABLE I

| Reagent | Dilutions of reference serum | | | | | | | | |
|---|---|---|---|---|---|---|---|---|---|
| | 1/10 | 1/20 | 1/40 | 1/80 | 1/160 | 1/320 | 1/640 | 1/1280 | 1/2560 |
| Sensitized cells, 1% in PBS | + | + | + | + | + | + | ± | ± | ± |
| Sensitized cells, 1% in PBS + serum albumin | + | + | + | + | + | + | − | − | − |

+: distinct hemagglutination
±: partial hemagglutination (unreadable)
−: absence of hemagglutination

EXAMPLE 3

Determination of antitetanus antibodies in blood

The blood sample is drawn by pricking the end of the finger with a vaccinostyle and 10 μl of this are diluted with 190 μl of distilled water.

In the first two cups, 50 μl of a 1/20 dilution of the blood are introduced, followed by 50 μl of diluent in cups 2 to 8. A geometric series of dilutions is then made in cups 3 to 11, in each instance introducing 50 μl from the preceding cup, except in cup No. 11, which leads to 50 μl being discarded from cup No. 10.

50 μl of sensitized cells obtained according to Example 1, in 1% suspension in phosphate-buffered saline, are added into each cup; the plate is agitated for one minute and left covered to incubate for approximately 15 minutes.

A series prepared with a reference antitetanus serum containing 1 IAU/ml, carried out simultaneously, shows that the limiting dilution of serum giving distinct hemagglutination (uniform network distributed over the whole cup) corresponds to a 1/2560 dilution of the serum, which corresponds to approximately 1 IAU/ml. Under these conditions, the dilution of the blood of an individual at the limit of protection against tetanus is present in cup No. 3, and corresponds to 0.032 IAU/ml of blood.

I claim:

1. A method of preparing a reagent for the determination of antibodies to a bacterial toxin for use in a hemagglutination assay consisting essentially of treating erythrocytes with glutaraldehyde and then with the bacterial toxin in the presence of glutaraldehyde without a washing step between the two steps.

2. The method of preparing the reagent as claimed in claim 1 further comprising:
treating the reagent obtained in claim 1 with a reagent for blocking aldehyde groups.

3. The method as claimed in claim 1, wherein
a) glutaraldehyde is reacted with a suspension of turkey blood erythrocytes in a buffered isotonic medium of pH 6.5 to 8 at a temperature of between room temperature and 37° C., such that the erythrocytes are present in the proportion of 0.75 to 8% (v/v) for a glutaraldehyde concentration of between 0.001M and 0.1M;
b) the toxin is reacted with the erythrocytes thereby obtained, in buffered isotonic suspension, for at least one hour in the presence of glutaraldehyde, in the proportion of 0.4 mg to 2 mg of toxin per ml of erythrocytes; and
c) the erythrocytes thus treated are washed to remove the excess reagents.

4. The method as claimed in claim 2, wherein the erythrocytes are further treated, after centrifugation for at least 15 minutes, with an equal volume of a buffered aqueous solution of glycine or lysine having a final concentration of between 0.1M and 1M.

5. The method as claimed in claim 1, wherein said bacterial toxin is tetanus toxin.

6. The method as claimed in claim 1, wherein said bacterial toxin is diphtheria toxin.

7. A non-toxic reagent for the determination of antibodies to a bacterial toxin for use in a hemagglutination assay wherein said reagent is made by binding said bacterial toxin to erythrocytes in the presence of glutaraldehyde and then detoxifying said bacterial toxin to form a toxoid without a washing step between the binding step and the detoxifying step.

8. The reagent as claimed in claim 7, which is further stabilized by treatment with an agent for blocking the glutaraldehyde.

9. The reagent as claimed in claim 7, wherein said bacterial toxin is tetanus toxin.

10. The reagent as claimed in claim 7, wherein said bacterial toxin is diphtheria toxin.

11. A method for determining the concentration of antibodies to a bacterial toxin in a sample comprising:
making dilutions of the sample in an aqueous buffer solution;
mixing the dilutions of the sample with the reagent as claimed in claim 7;
observing the dilutions at which hemagglutination occurs; and
comparing the results with the results obtained using a reference standard to determine the concentration of antibodies in said sample.

12. The method as claimed in claim 11, wherein the sample to be assayed is whole blood.

13. The method as claimed in claim 11, wherein said antibodies are antitetanus toxin antibodies.

14. The method as claimed in claim 11, wherein said antibodies are anti-diphtheria toxin antibodies and wherein human serum albumin is mixed with the dilutions of the sample and the reagent of claim 7.

15. A non-toxic reagent for the determination of antibodies to a bacterial toxin for use in a hemagglutination assay consisting essentially of erythrocytes to which a toxoid corresponding to the bacterial toxin is chemically coupled by glutaraldehyde, the toxoid resulting from modifying the structure of the bacterial toxin by glutaraldehyde thereby causing a loss of its toxic activity towards warm-blooded animals without denaturing the antigenic sites of the bacterial toxin.

16. A reagent kit for determination of antibodies to a bacterial toxin for use in a hemagglutination assay comprising: a) a plate containing a plurality of wells, b) the reagent of claim 7 in an aqueous buffered suspension containing erythrocytes having the bacterial toxin bound thereto and a preservative, c) a buffered aqueous solution for diluting samples, and d) a reference serum containing a known concentration of antibodies to the bacterial toxin.

* * * * *